United States Patent [19]

Welker

[11] Patent Number: 4,525,127
[45] Date of Patent: Jun. 25, 1985

[54] FLUID PUMP MECHANISM

[75] Inventor: Robert H. Welker, Sugar Land, Tex.

[73] Assignee: Welker Engineering Company, Sugar Land, Tex.

[21] Appl. No.: 222,362

[22] Filed: Jan. 5, 1981

[51] Int. Cl.$^3$ ............................................. F04B 43/06
[52] U.S. Cl. ................................ 417/479; 73/863.84; 92/90; 417/501
[58] Field of Search ................... 417/479, 480, 501; 92/89, 90; 73/863.83, 863.84, 864.34

[56] References Cited

U.S. PATENT DOCUMENTS

| | | | |
|---|---|---|---|
| 1,756,678 | 4/1930 | Cumming | 417/479 |
| 2,929,332 | 3/1960 | Pierce | 417/479 X |
| 3,270,684 | 9/1966 | Pasquali et al. | 92/90 |
| 3,945,770 | 3/1976 | Welker | 417/479 X |

FOREIGN PATENT DOCUMENTS 97627  4/1961  Netherlands ........................ 417/479

OTHER PUBLICATIONS

Welker Engineering Company, Bellaire, TX.

Primary Examiner—Richard E. Gluck
Attorney, Agent, or Firm—Gunn, Lee & Jackson

[57] ABSTRACT

A vanishing chamber type positive displacement pump is disclosed which is applicable for use as a fluid sampling device for sampling liquid or gaseous materials from pipelines or other pressurized vessels or for pumping small measured quantities of fluid from a source such as for chemical or other fluid injection. The pump mechanism incorporates a support body structure that is adapted for connection to an isolation valve such as for pipeline or pressurized vessel sampling or is adapted for direct connection to the wall structure of a vessel if desired. An elongated probe is movable connected in sealed relation to the support body structure and is capable of being inserted into the pipeline or other vessel being sampled. The elongated probe is provided with a housing at the free extremity thereof within which is located a positive displacement pump having an inlet defined by the housing which is located at the free extremity of the housing. This feature enables positioning of the inlet at an optimum sampling position within a pipeline so that interference with fluid flowing through the pipeline will be minimized. The probe and the pumping mechanism or probe transducer is also capable of being withdrawn from the pipeline and retracted into a protective environment so that it does not interfere with movement of objects such as pigs or scrapers passing through the pipeline.

9 Claims, 5 Drawing Figures

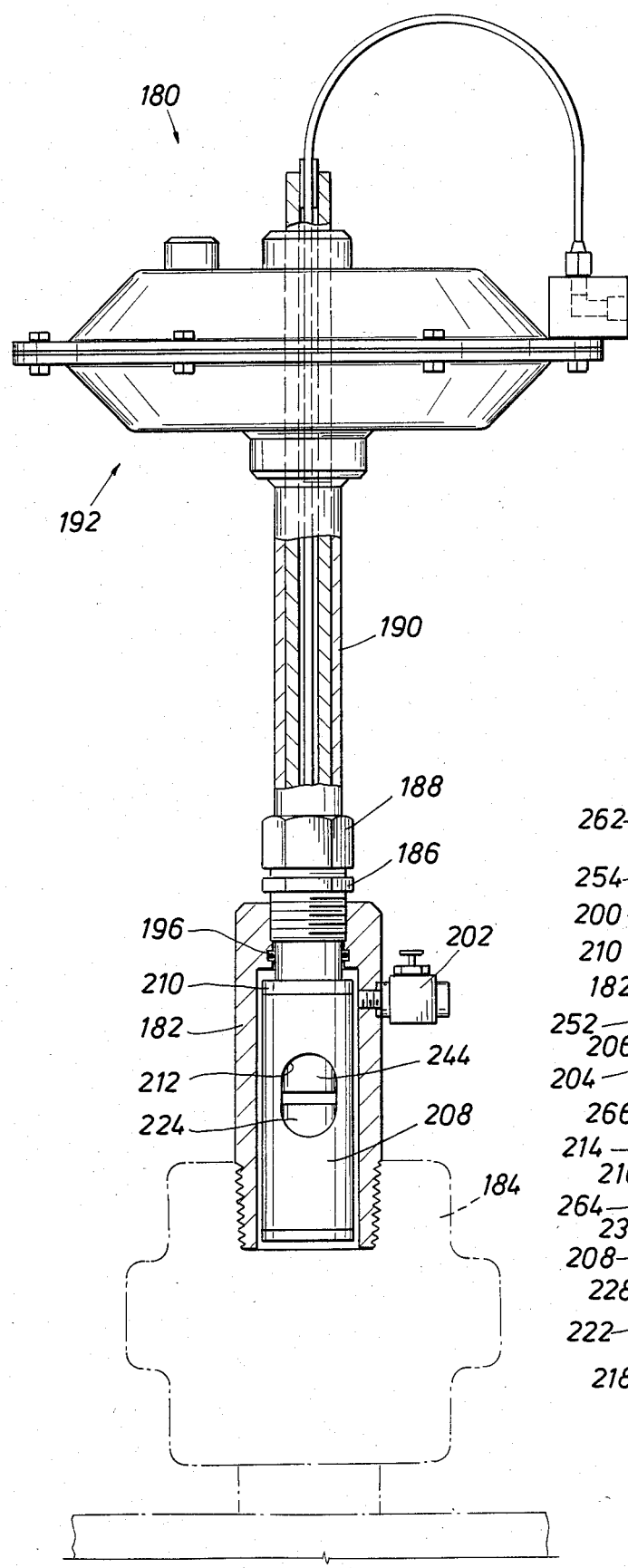
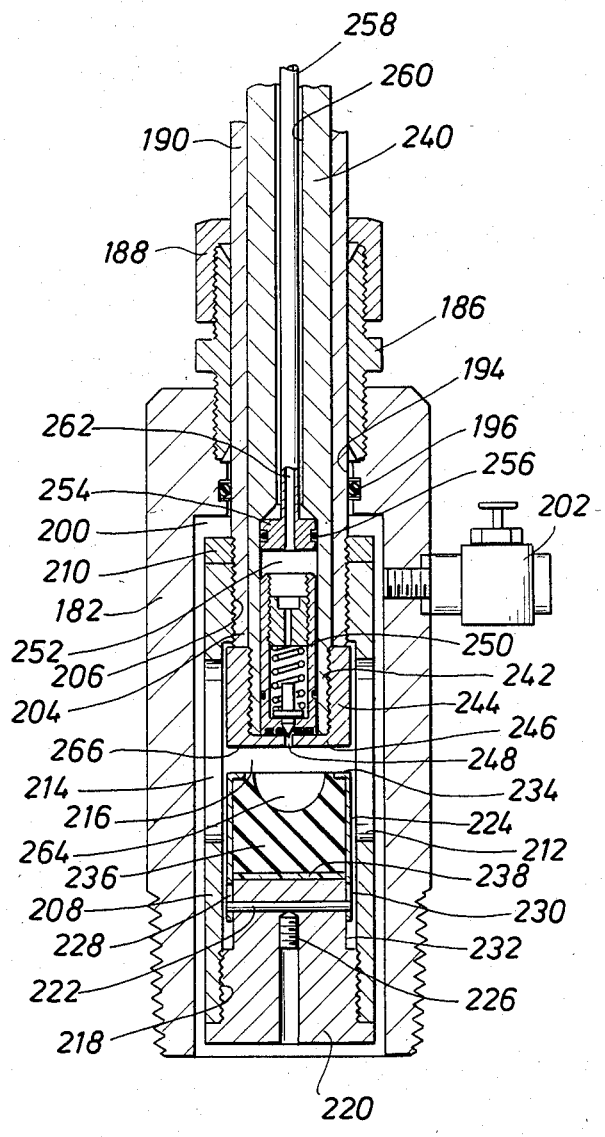
FIG. 4
FIG. 5

# FLUID PUMP MECHANISM

FIELD OF THE INVENTION

This invention relates generally to the transfer of measured quantities of fluid from a fluid source wherein the fluid being transferred may take the form of a fluid sample that may be investigated or, alternatively, may take the form of a measured fluid supply for any suitable use. More specifically, the present invention is directed to the provision of a movable probe incorporating a pumping head or transducer that is extendable into a fluid handling system and achieves pumping activity by mechanical displacement of a body of elastomeric material. Even further, the present invention is directed to the provision of a pumping mechanism having the capability of pumping measured quantities of fluid from an environment where wide pressure variations may be encountered.

BACKGROUND OF THE DISCLOSURE

In many pipelines where flowing gaseous or liquid products are handled and controlled, it is necessary to accomplish a wide variety of fluid measurement during the various aspects of fluid processing. Typical fluid measurements include measurement of the pressure of the fluid and measurement of the volume of fluid flowing at any given time. In many cases, it is also desirable to take periodic samples of the flowing fluid to insure that processing personnel remain continuously aware of the various characteristics of the fluid and any changes that may occur as the fluid is processed. From the standpoint of sampling, in many cases it is desirable to frequently sample process fluid that is contained within a process vessel other than a pipeline. It is desirable, therefore, to provide means for extacting measured quantities of fluid from process vessels in simple and efficient manner. It is also desirable to insure that the sample extracting apparatus be capable of being separated from the process vessel or pipeline without requiring shutting down of the process involved.

It is well known that liquid products contained within process vessels or flowing through pipelines tend to stratify based on the weight of the molecules from which the process fluid is composed. Accordingly, heavier molecules settle to the bottom of the pipeline or process vessel and lighter molecules tend to rise to the upper portion of the fluid. If a fluid sample is taken from the upper most or lower most parts of the pipline or process vessel, the sample so taken may not be truly representative of the average nature of the fluid product involved. For example, in the event the fluid is a hydrocarbon product, the upper portion of the process vessel or pipeline may tend toward the lighter ends of the hydrocarbon product. Conversely, a sampler positioned with its inlet at the very bottom of the pipe may tend to distort the data by yielding a sample having a larger number of heavy molecules. It is desirable, therefore, to provide sampling apparatus that is enabled to take samples from the central portion of the pipeline or process vessel to thereby insure that the sample accurately conforms to the average of the process fluid.

From the standpoint of taking samples from pipelines, it should be borne in mind that it is typical, in many cases, to pass pipelines pigs or scrapers through the pipe to remove accumulation of material adhering thereto. In the event a pipeline sampling device extends into the pipe, it would intereferre with passage of the pig or scaper. It is, therefore, desirable to provide a sampling device that may be utilized in conjuction with pipelines and which has the capability of being retracted from the flow way of the pipeline under circumstances where pigs, scrapers or other devices are passed through the pipe for cleaning or other servicing operations. It is also desirable that the sampling device be capable of being retracted from the flow way of the pipe without requiring the fluid processing system to be shut down.

In many cases, process piping is of quite small dimension. Even though sampling probes or transducers may be of relatively small dimension, the probe apparatus may create substantial interference with the flowing fluid when emplaced within the flow way of small pipes. It is, therefore, desirable to provide a fluid sampling transducer having the inlet thereof located at the free extremity of the transducer so that only a small portion of the transducer is positioned in the flowing fluid. In the apparatus of this invention only, the free extremity of the probe need be positioned near the center of the flow way in order to achieve optimum sampling and yet the transducer does not interfere materially with the flow of fluid.

THE PRIOR ART

In the past, transducer probes have been developed having the capability of being inserted into and withdrawn from a process system such as a pipeline, as indicated by U.S. Pat. No. 4,177,676 of common inventorship herewith. Further, pumping mechanisms incorporating the deformable elastomeric material have also been developed as set forth in U.S. Pat. No. 3,945,770, also of common inventorship herewith. Attention is also directed to Netherlands Pat. No. 97,627 of Apr. 17, 1961 which discloses compression of a fluid medium by means of mechanical deformation of an elastomeric material. Additionally, German Pat. No. 1,453,608 of Dec. 2, 1963 and corresponding U.S. Pat. No. 3,270,684 discloses similar deformation of elastomeric material for modification of the volume of a pumping chamber. Australian Pat. No. 209,227 of July 5, 1956 and corresponding U.S. Pat. No. 2,929,332 also teaches pumping by means of volumetric changes induced mechanically to a body of elastomeric material.

The present invention represents an improvement over previously known pumping and sampling apparatus and involves a pumping or sampling probe that includes a probe shaft which is capable of being extended into a pipeline or process vessel and selectively retracted therefrom without necessitating shutting down of the process being conducted. A pump mechanism or transducer is connected to the inner, free extremity of the probe shaft and is arranged so that the inlet thereof is located at the free extremity of the transducer. This feature enables the transducer to be positioned with the inlet at the center portion of the pipeline or at an appropriate selected portion of the process vessel, thereby insuring that an otimum sample is taken and further insuring that the transducer repesents minimal interference to flowing or other handling of the process fluid.

BRIEF DESCRIPTION OF THE DISCLOSED APPARATUS

The fluid sampler or pumping mechanism of the present invention is adapted to be connected to an isolation valve which is in turn interconnected with a pipeline or process vessel from which the sample or measured unit of fluid is to be taken. The apparatus incorporates a mounting base structure that defines an internal chamber within which the pumping housing or transducer portion of the apparatus may be retracted. The apparatus incorporates an elongated tubular probe which is sealed with respect to the connecting base portion of the apparatus by means of a packing gland. The tubular probe is adapted to be moved linerally with respect to the connecting base portion while maintaining this sealed relationship. For sampling, with the isolation valve open, the probe is moved linerally into the pipeline or process vessel. A transducer housing is provided at the inner, free extremity of the tubular probe and defines inlet means by which fluid is enabled to enter the transducer. In one form of the invention, to minimize interference with flow in the event the transducer is adapted to be disposed within a flow way of a pipeline, the inlet is disposed adjacent the free extremity of the transducer. This enables the inner extremity of the transducer to be positioned at the optimum position for sampling, thereby locating the inlet opening at this optimum position.

Within the transducer housing is provided a body of elastomeric material having a pumping cavity formed at one side thereof, which cavity faces a wall that is defined by the transducer. This body of elastomeric material is supported by means of an inner tubular member that extends through the tubular probe and is capable of linear movement therein. Force inducing apparatus such as a pneumatic or hydraulic motor or any other suitable power mechanism is interconnected with the inner tubular member and, upon being energized, causes linear movement of the inner tubular member within the tubular probe. This movement causes the elastomeric body to be forced against the wall member of the transducer with sufficient magnitude that the elastomeric material is deformed to the extent that the cavity is completely displaced by the elastomeric material. When this occurs, the fluid contained within the cavity is first entrapped against the wall member, thereby defining a measured quantity of fluid. Upon complete displacement of the cavity by the elastomeric material, the fluid so entrapped, is forced through a valve controlled passage of the inner tubular member and is conducted through this passage for subsequent use in the desired manner. A valve mechanism is incorporated within the transducer and is maintained closed against the pressure of the process fluid by means of suitable urging means. As the pumping cavity is deformed by the elastomeric material, fluid contained within the pumping cavity is subjected to sufficiently increased pressure to overcome the urging means, unseat the valve and allow flow of fluid from the pumping cavity to the flow passage of the inner tubular member. In one embodiment, the wall member is defined by the transducer housing and fluid pumped from the pumping cavity passes through the elastomeric material to the pumping valve. In an alternative embodiment, the elastomeric body of material is supported by the transducer housing structure and the inner tubular member with its valve mechanism moves against the body of elastomeric material with sufficient force to deform the elastomeric material and completely displace the pumping cavity.

BRIEF DESCRIPTION OF THE DRAWINGS

So that the manner in which the above recited features, advantages and objects of the invention, as well as others, which will become apparent, are attained and can be understood in detail, a more particular description of the invention, briefly summarized above, may be had by reference to the embodiments thereof that are illustrated in the appended drawings, which drawings form a part of this specification. It is to be noted, however, that the appended drawings illustrate only typical embodiments of the invention and are not to be considered limiting of its scope, for the invention may admit to other equally effective embodiments.

IN THE DRAWINGS

Figure 1:
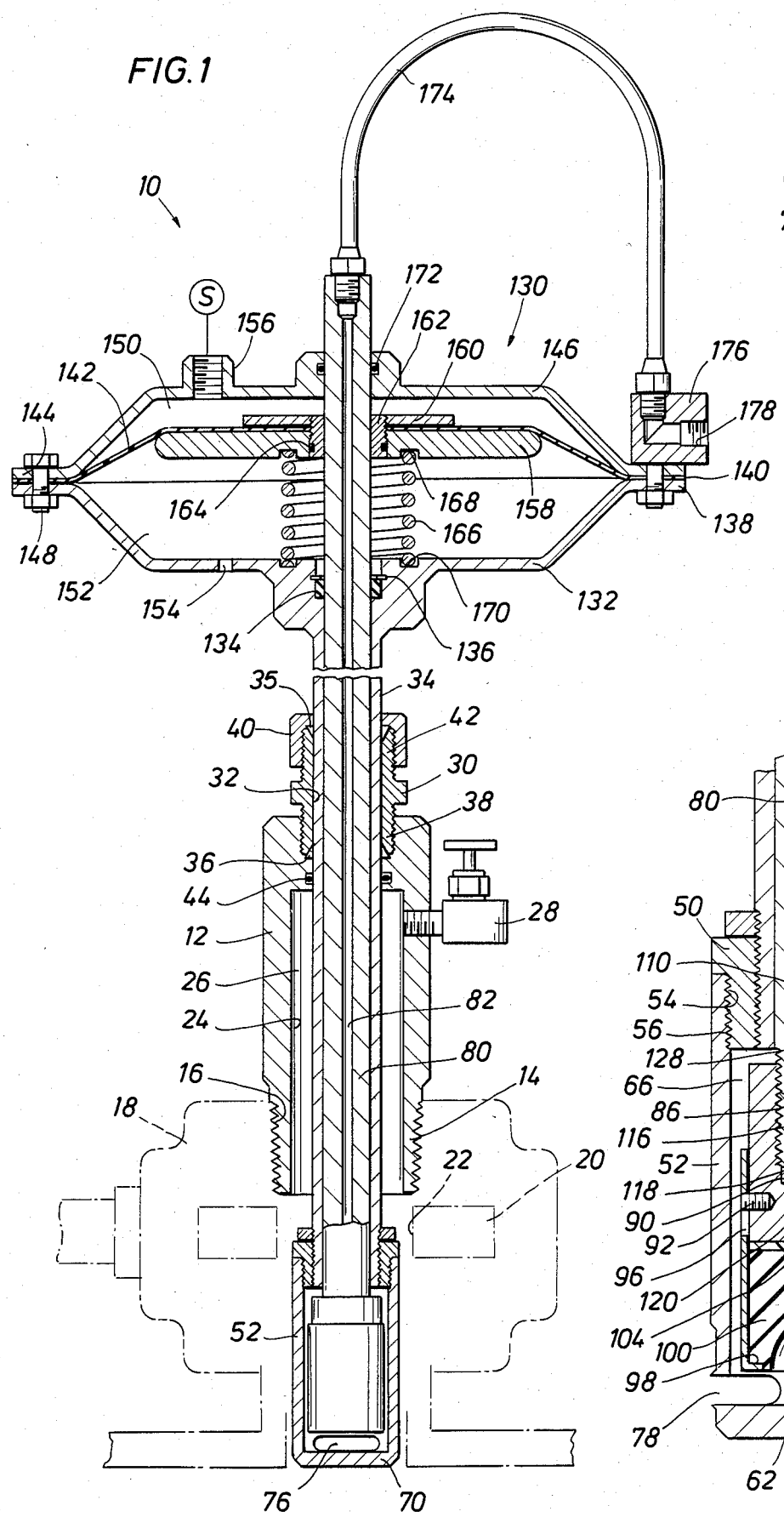

FIG. 1 is a sectional view of pumping and sampling apparatus constructed in accordance with the present invention and illustrating connection of the apparatus to an isolation valve that is in turn interconnected with a process vessel or pipeline.

Figure 2:
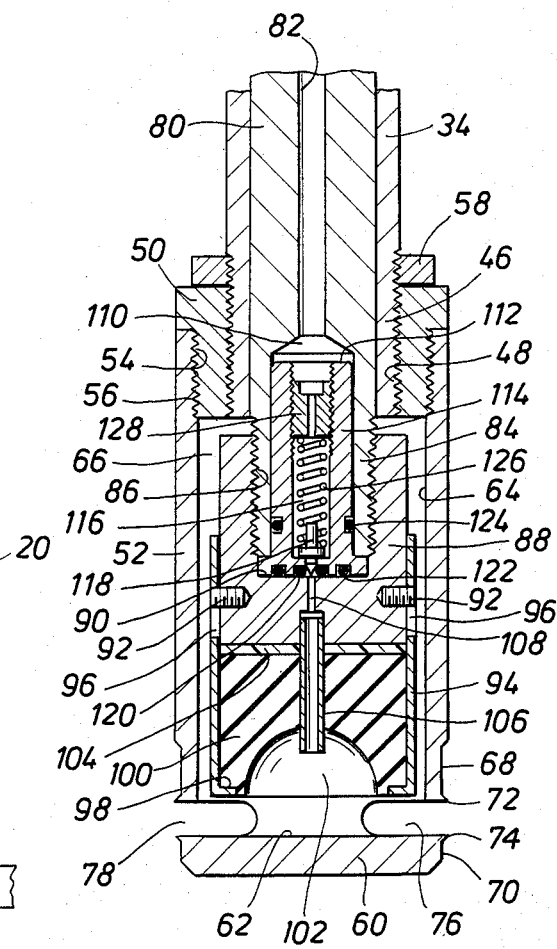

FIG. 2 is a fragmentary sectional view of the apparatus of FIG. 1 illustrating the structural features of the pumping tansducer in detail.

Figure 3:
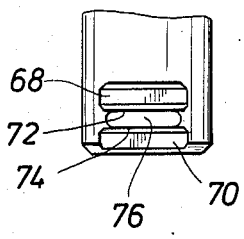

FIG. 3 is a side view of the lower portion of the pump housing of FIG. 1, illustrating the form and structure of the inlet portion of the pump housing.

FIG. 4 is a sectional view of a pumping and sampling transducer that represents an alternative embodiment of the present invention and also discloses the apparatus in connection with an isolation valve and with the pumping and sampling transducer thereof retracted within the protective receptable thereof.

FIG. 5 is a fragmentary sectional view of the apparatus of FIG. 4 illustrating the internal components of the pumping and sampling transducer in detail.

DETAILED DESCRIPTION OF PREFERRED EMBODIMENT

Referring now to the drawings and first to FIG. 1, a fluid pumping and sampling mechanism is illustrated generally at 10 and incorporates a connection body structure 12 having a lower threaded extremity 14 that is adapted to be received in threaded engagement with an internally threaded portion 16 of an isolation valve 18 shown in broken line. The isolation valve 18 is shown to be a gate valve with the gate 20 thereof disposed in its open position with the port 22 of the gate being disposed in registry with an internal cylindrical surface 24 that defines a protective receptacle 26 within the connection body structure. A bleed valve 28 which is connected in any suitable manner to the connection body structure 12 is enabled to bleed the protective receptable 26 and thereby disapate pressure therefrom under circumstances where the pumping and sampling transducer is retracted within the protective receptable and the gate element 20 of the valve 18 is closed. In the position illustrated in FIG. 1, however, the gate 20 must be opened since the pumping and sampling transducer portion of the apparatus is extended through the port of the gate.

At the upper portion of the connection body 12 is provided a packing adapter 30 which is threaded into the upper portion of the connection body. The packing adapter defines a passage 32 through which an elongated tubular transducer probe extends. The probe 34 is linerally movable with respect to the packing adapter and is sealed with respect to the packing adapter by means of upper and lower annular sealing elements 35 and 36. The sealing elements 35 and 36 are annular sealing elements of generally triangular cross-sectional configuration. The lower sealing element 36, which may be formed of polytetrafluoroethylene or any other suitable sealing material having low friction characteristics, is retained within the connection body structure by the internally beveled lower extremity 38 of the packing adapter. A packing retainer 40, which is received about the tubular transducer probe 34 and is received in threaded engagement with the upper extremity 42 of the packing adapter, functions to retain the annular sealing element 35 in sealed assembly with respect to the packing adapter and the transducer probe. The sealing element 35 may be composed of stainless steel or any other suitable metal sealing material in order to provide the transducer probe mechanism with high pressure sealing capability. Obviously, any other suitable sealing material may be utilized for the upper annular sealing element 35 within the spirit and scope of the present invention.

The packing adapter 30 and the packing retainer 40 provide effectively for securing the transducer probe 34 in immovable relation with respect to the connection body structure 12. For movement of the transducer probe, the packing adapter 40 will be backed off sufficiently to release mechanical pressure acting on the annular sealing element 35. After this has been done, the tubular transducer probe may be moved inwardly or outwardly as desired either to position the pumping and sampling transducer within a pipeline or process vessel as desired or retract the transducer within the protective receptable 26. After positioning of the transducer probe has been accomplished, the packing retainer 40 then may be threaded into tightly secured relationship with respect to the packing adapter and the tapered upper sealing ring 35 to establish sufficient frictional contact with the transducer probe to retain it in fixed relation with the packing adapter and connection body. Sealing of the tubular transducer probe with respect to the connection body structure 12 is enhanced by means of an annular sealing element 44 which is retained within an appropriate annular groove defined within the connection body. The transducer probe, therefore, may be moved inwardly or outwardly as desired while maintaining sealing engagement between the transducer probe and connection body to prevent leakage during movement of the probe.

The transducer probe is provided with an externally threaded lower extremity 46 which is received by internal threads 48 defined by a transducer housing adapter 50. A transducer housing 52 is formed to define an internally threaded upper extremity 54 which is received by external threads 56 defined on the transducer housing adapter. A lock member 58 is also received by the externally threaded lower portion 46 of the transducer probe and functions to lock the housing adapter 50 in positively secured, immovable relation with respect to the lower portion of the transducer probe. The transducer housing 52 is closed at its lower extremity by a wall structure 60 which defines a substantially planar circular surface 62. The circular surface 62, together with the internal cylindrical surface 64 defined by the transducer housing 52, define a pumping chamber 66.

Since the fluid is pumped from the pumping chamber, it is necessary that the transducer housing be provided with inlet openings in order that fluid will enter the pumping chamber. As mentioned above, it is also desirable that fluid be capable of entering the pumping chamber at the free extremity of the transducer probe structure. By locating the inlet openings of the pumping chamber at the free extremity of the transducer housing, sufficient fluid samples may be taken from stratified pipeline systems without developing material interference with the flow of fluid through the flow way defined thereby. In other words, location of the inner extremity of the transducer probe at the center portion of a pipeline will place the inlet openings at the center portion of the pipeline. This enables accurate samples to be taken and yet the transducer housing does not materially interfere with flow of fluid through the pipeline. As shown in the drawings and in detail in FIGS. 2 and 3, the upstream portion of the transducer housing is deformed by means of upper and lower transverse cuts as shown at 68 and 70 thereby defining relatively sharp knife edges or lips 72 and 74 on either side of an inlet opening 76. The cuts 68 and 70 may be formed by milling flats on the cylindrical housing 52 and the inlet opening 76 may be in the form of an elongated transverse slot that is also formed by a milling cutter or drill. The housing struture 52 is also formed to define at least one outlet opening 78 which may be drilled or otherwise formed in the housing structure. The purpose of the relatively sharp edges 72 and 74 above and below the inlet opening 76 is to allow efficient flow of fluid through the housing. The knife edges 72 and 74 part or shear the fluid while at the same time minimizing turbulance that is developed at the inlet. Therefore, flowing fluid passes into the pumping chamber in relatively undisturbed manner thereby rendering sampling more efficient and accurate.

An elongated inner tubular member is positioned within the tubular transducer probe 34 and is capable of linear movement therein. The inner tubular member defines an internal passage 82 that extends substantially the entire length thereof. As shown in detail in FIG. 2, the lower extremity 84 of the internal tubular member is externally threaded and receives internal threads 86 defined within an anvil structure 88. The lower extremity of the internally threaded opening 86 of the anvil is defined by a substantially planar circular surface 90 that defines a sealing surface as will be discussed hereinbelow. Two or more opposed retainer devices 92 which may take the form of set screws are received within appropriate openings defined within the anvil 88 and provide guiding support for a generally cylindrical hanger bracket 94. The set screws 92 extent through opposed elongated openings or slots 96 defined in the hanger bracket, thereby allowing the hanger bracket to be capable of linear movement relative to the anvil structure within limits defined by the length of the elongated openings or slots 96.

The hanger bracket 94 is turned inwardly at the lower portion thereof defining an inwardly extending annular flange 98. A generally cylindrical body 100 of elastomeric material is retained within the hanger bracket 94 and is supported by means of the annular flange 98 and by the wall surfaces of the hanger bracket. The lower portion of the body of elastomeric material is formed to define a generally hemispherical pumping cavity 102 that opens towards to planar surface 62 defined by the wall structure 60. A low friction washer which is composed of a material such as polytetrafluoroethylene or the like is interposed between the anvil 88 and the body of elastomeric material 100. A fluid communicating tube 106 extends through an aligned passage defined in the elastomeric material 100, the friction resistent washer 104 and the lower portion of the anvil 88. The tube 106 defines a passage that communicates with a connecting passage 108 extending to a valve chamber 110 which is in communication with the pump discharge passage 82. Within the valve chamber 110, is located an inline relief valve 112 that incorporates a valve body 114 forming a valve cavity 116 within which is located a check valve 118. A conical lower portion of the valve 118 extends through a valve aperture formed in the lower portion of the valve body 114 and is capable of establishing a seal with an annular seat member 120 and is retained within a sealed receptacle defined at the lower portion of the valve body. The annular sealing element 120, which may be in the form of an O-ring or any other suitable annular sealing element, surrounds the upper opening of passage 108 and establishes a seal with the planar sealing surface 90. This sealing element thus confines fluid pressure at the lower portion of the valve mechanism and insures that upwardly flowing fluid from the passage 108 enters past the check valve 118 into the valve chamber 116. Additional sealing at the lower portion of the valve mechanism 112 is established by an additional sealing ring 122 that is disposed in concentric relation with the sealing ring 96. Each of the sealing rings 120 and 122 may be composed of any suitable elastomeric material if desired, or, in the alternative, may conveniently take the form of sealing material of plastic nature such as polyetrafluoro ethylene or other suitable sealing material. Sealing of the valve body structure 114 relative to the inner tubular member 80 is established by means of an annular sealing element 124 which is retained within a suitable annular groove formed in the outer periphery of the valve body.

The check valve element 118 is urged into sealing relationship with the annular sealing element 120 by means of a compression spring 126 that is retained within the valve chamber 116 by means of a retainer element 128 which is threaded into the upper portion of the valve body. The retainer element 128 may be positioned within the valve body such that the compression spring 126 is maintained under suitable compression to control the opening pressure of the check valve 118. Typically, the spring pressure of spring 126 is set such that the check valve 118 opens at a pressure slightly above the highest pressure that is expected in the pipeline or pressure vessel within which the probe is to be located. The pressure of the process or pipeline, therefore, is unable to unseat the valve 118 and allow inadvertent flow of fluid from the process through the discharge pasage 82.

As mentioned above, the inner tubular member 80 is movable within the outer tubular transducer probe 34. As the inner tubular member 80 is moved downwardly, the lower portion of the elastomeric body 100 and the lower portion of the hanger bracket 94 will come into contact with the planar surface 62 of the housing 52. Continued forceable downward movement of the inner tubular member relative to the transducer probe and probe housing will result in deformation of the elastomeric material 100 as the anvil 88 is driven downwardly by the inner tubular member. The hanger bracket 94 will cease downward movement at this point since it is composed of fairly rigid material. As the anvil 88 continues to move downwardly, the set screw stop members 92 will move downwardly through the guide slots 96 as the elastomeric material continues to be deformed. As the elastomeric material deforms, the pumping cavity 102 is displaced by the elastomeric material thereby reducing or completely displacing the dimension of the cavity. Since the lower portion of the elastomeric body will be in contact with the planar sealing surface 62, fluid will be entrapped within the cavity 102. As the cavity diminishes in volume, this entrapped fluid will be forced through tubular member 106 and through passage 108 upwardly to the check valve 118. As soon as the pressure within the cavity 102 exceeds the pressure for which the compression spring 126 is set, the check valve 118 is unseated and flow of fluid is allowed from the passage 108 past the valve into the valve chamber 116 and thence through the passage of the spring retainer 128 and into the discharge passage 82.

As the elastomeric member 100 is deformed against the surface 62 by downward movement of the anvil 88, the elastomeric material functions in fluid like manner. The tubular member 106 resists collapse of the opening extending through the elastomeric material. The lower extremity of the tubular member 106 extends well into the cavity 102 to accommodate the material displacing the cavity. Downward movement of the anvil is such, however, that the lower extremity of the tubular member does not come into contact with the planar surface 62.

It is desirable to provide means for imparting downward and upward movement to the inner tubular member 80 to achieve pumping of fluid from the fluid source through the discharge passage 82. According to the present invention, one suitable means for accomplishing controlled movement of the inner tubular member may conveniently take the form of a fluid energized diaphragm motor such as shown in the upper portion of FIG. 1. Obviously, other mechanical apparatus may be employed within the spirit and scope of this invention for the purpose of moving the inner tubular member. A shown in FIG. 1, the motor mechanism is illustrated generally at 130 and incorporates a dished body structure 132 that is suitably connected to the upper portion of the outer tubular transducer probe 34. The inner tubular member extends through the body structure 132 and is sealed with respect to the body structure by means of a packing element 134 that is retained within a packing chamber by means of a retainer element 136. The body structure 132 is of generally circular dished form and defines a circular support flange 138 against which is seated the peripheral portion 140 of a diaphragm 142. The periphery of the diaphragm is retained in assembly with the flange 138 by a retainer flange 144 that forms the outer peripheral portion of a diaphragm housing 146. A plurality of bolts 148 or other suitable connectors extend through the flanges 138 and 144 and function to secure the flanges in positive sealed assembly with one another and with the peripheral portion 140 of the diaphragm which is interposed therebetween. The diaphragm 142 cooperates with the motor body structure 132 and the diaphragm housing 146 to define a power chamber 150 and a spring chamber 152. The spring chamber is vented to the atmosphere by means of one or more vent ports 154 and the spring chamber is therefore maintained at ambient pressure at all times. The diaphragm housing 146 is formed to define an internally threaded connector 156 to which is adapted to be connected a supply tube extending from any suitable source S of pneumatic fluid. Although the mechanism is shown to be a pneumatically energized motor, it should be understood that hydraulically energized motors or other mechanical motor systems may be utilized within the spirit and scope of this invention. A diaphragm plate 158 is located within the diaphragm chamber and is retained in assembly with the diaphragm 142 by means of a diaphragm retainer element 160. The retainer element 160 is secured to the diaphragm plate 158 by means of a transition member 162 that is sealed with respect to the diaphragm plate by means of an O-ring type seal 164 or any other suitable sealing element. A compression spring 166 is positioned within the spring chamber 166 with upper and lower extremities thereof being disposed within spring retainer grooves 168 and 170 that are defined respectively in the diaphragm plate 158 and the body structure 132. An annular sealing member 172 is provided to establish a positive seal between the diaphragm housing 146 and the inner tubular member 80, thus eliminating leakage from the power chamber 150 as the power chamber is energized.

Controlled operation of the diaphragm motor 130 is achieved by introduction of pressurized fluid medium from the source S under any suitable control. As pressure increases within the diaphragm chamber 150, the differential developed with respect to ambient pressure in the chamber 152 allows a downward resultant force to be developed on the diaphragm thereby urging the diaphragm downwardly. Since the diaphragm plate assembly is secured to the inner tubular member, this force also drives the inner tubular member downwardly to achieve pumping at the free extremity of the probe. After the elastomeric material 100 has been completely deformed, diminishing the volume of the pumping cavity to zero or near zero, a power pumping stroke has been completed. The pressure within the power chamber 150 will then be allowed to dissipate and the compression spring 166 will then urge the diaphragm plate 158 and the inner tubular member upwardly, thus preparing the pumping mechanism for a subsequent power stroke. The pumped fluid medium will pass through the discharge passage 82 of the inner tubular member and will then enter a flexible tube 174 which conducts the pumped fluid to a fluid discharge structure 176. Any suitable supply tube 178, connected to the structure 176, may be employed to conduct the pumped fluid medium to other desired apparatus.

As illustrated in FIGS. 4 and 5, the pumping mechanism may take another convenient form. The pumping mechanism illustrated in FIGS. 4 and 5 may be employed under circumstances where it is not necessary to locate the inlet and outlet portions of the pump at the free extremity of the pumping transducer. The apparatus of FIG. 3 is illustrated generally at 180 and incorporates a connection body structure 182 that is adapted for connection to an isolation valve 184 in the same manner as discussed above in conjunction with FIG. 1. A packing adapter 186 is secured to the upper portion of the connection body 182 and incorporates a packing retainer element 188 which may be of identical construction as compared to the packing retainer and seals discussed above in connection with FIG. 1. An outer tubular member 190 extends through the packing adapter 186 and is adjustably positionable with respect to the packing adapter in the same manner as discussed above. The tubular transducer probe 190 is secured to the lower portion of a diaphragm motor 192 that may also be identical with respect to the motor mechanism shown in FIG. 1.

The outer tubular transducer probe 190 extends through a passage 194 formed in the connection body 182 and is sealed with respect to the connection body by means of an annular sealing element 196 that is positioned within an annular packing chamber formed internally of the connection body. The connection body is also formed internally to define a protective receptacle 200 within which a pumping transducer disposed at the free extremity of the transducer probe 190 may be retracted under circumstances where isolation of the pumping probe is desired. Again, it should be borne in mind that the isolation valve 184 will be closed when the pumping transducer is positioned as shown in FIGS. 4 and 5 thus isolating the pumping transducer from the fluid of the process. A vent valve 202 is secured to the connection body and may be opened for the purpose of venting the receptacle 200 after the isolation valve has been closed.

The lower extremity of the tubular transducer probe 190 is formed to define an externally threaded portion 204 which is received by the upper internally threaded portion 206 of a pump body structure 208. A locking element 210 is also secured to the lower threaded portion of the probe 190 and functions to lock the pump body with respect to the probe. The pump body is formed to define opposed elliptical inlet and outlet openings 212 and 214 that allow process fluid to enter a pump chamber 216 defined within the pump housing. The lower portion of the housing 208 is formed to define an interally threaded portion 218 within which is located a retainer plug 220. A guide pin 222 is positioned within a transverse bore extending through the retainer plug with end portions thereof exposed for guiding relation with a support bracket 224. The guide pin 222 is secured with respect to the plug 220 by means of a set screw or the like 226. The support bracket is formed to define opposed elongated guide slots 228 and 230 that receive respective extremities of the guide pin 222 and thus allow the support bracket 224 to have limited movement relative to the plug 220 within limits defined by the length of the guide slots. The support bracket is movable relative to an upwardly projecting reduced diameter portion 232 of the plug 220. The support bracket is formed to define an inwardly extending annular flange 234 at the upper portion thereof which functions as a retainer flange to retain a body 236 of elastomeric material in assembly with the support bracket. A low friction spacer 238 is interposed between the upper extremity of the plug 220 and the body of elastomeric material and functions to allow relatively free linear movement of the supper bracket relative to the plug as the elastomeric material 236 is deformed. An inner tubular member 240 is movably positioned within the tubular transducer probe 190 and defines a lower externally threaded extremity 242 about which is received a valve support end cap 244 having an internally threaded opening. The valve support cap 244 defines a closed lower end wall 246 having a small centrally located valve inlet opening 248 formed therein. The transverse wall 246 of the end cap defines a generally planar circular surface against which is seated a pair of concentric sealing rings retained within annular recesses formed in the lower portion of a valve mechanism 250. The valve mechanism 250 may be of the same general character and function as the valve mechanism 112 of FIG. 2. The inner tubular member 240 is formed to define an internal chamber 252 within which the valve mechanism 250 is retained by the end cap 244. The movable internal components of the valve mechanism 250 may be of essentially identical character with the valve mechanism 112 of FIG. 1. The external configuration of the valve body may differ in any suitable manner as shown. Additionally, within the valve chamber 252 is located a sealing spool or piston 254 that is sealed with respect to the wall surface of chamber 252 by means of an annular sealing element 256 that is retained within a groove formed therein. An elongated fluid conducting tube 258 extends through a passage 260 defined within the internal tubular member 240. Tube 258 is interconnected with the spool or piston 254 and the internal passage 262 of the tube is in communication with the valve chamber 252.

For purpose of achieving pumping operations, the inner tubular member 240 is moved downwardly by the diaphragm motor 192 in the same manner as discussed above in connection with FIG. 1. A generally planar lower surface 266 of the end cap 244 forms an anvil and moves into engagement with the upper portion of the elastomeric body 236 and support bracket 224, thus entraping a quantity of fluid within a pumping cavity 264 that is defined by the elastomeric body. As downward movement of the inner tubular member 240 continues, the support bracket 224 will be driven downwardly relative to the plug 220 and this downward movement will be accommodated by the guiding relationship of guide pin 222 with the opposed guide slots 228 and 230. Upon such further downward movement of the inner tubular member and the end cap, the elastomeric body 236 will be deformed, thereby causing the pumping cavity 264 to also be deformed. This deformation reduces the volume of the pumping cavity 264 and causes entrapped fluid therein to be forced through valve inlet opening 248 and past the check valve member of the valve mechanism. Downward movement of the end cap 244 will continue until such time as the cavity 264 has been completely displaced and thereby a measured quantity of fluid has been displaced or pumped from the cavity through the opening 248 and valve 250 into the discharge passage 262 of the tube 258. After a power pumping stroke has been completed, the pressure of the energizing fluid of the pneumatic or hydraulic actuator will be depleated, thereby allowing the internal compression spring of the actuator to move the inner tubular member upwardly, thus moving the end cap 244 upwardly to the position illustrated in FIG. 4.

Having thus described my invention in detail, I claim:

1. A pump mechanism for pumping measured quantities of fluid, said pump mechanism comprising:
   (a) body means adapted to support said pump mechanism and defining an internal receptacle open at one extremity thereof;
   (b) probe means extending in movable sealed relation through said body means, said probe means defining flow passage means;
   (c) transducer housing means being supported by said probe means and having a free extremity capable of being extended into a body of fluid to be pumped, said transducer housing means defining pump chamber means therein and further being receivable in protected relation within said internal receptacle of said body means;
   (d) wall means being defined at said free extremity of said transducer housing means and forming a wall of said pump chamber means;
   (e) a body of elastomeric material being movably positioned within said pump chamber means of said probe means and defining a pumping cavity opening toward said wall means, said body of elastomeric material further defining pumping passage means extending therethrough and communicating with said pumping cavity;
   (f) opposed elongated inlet and outlet openings being formed in said transducer housing and being oriented in substantially parallel relation with said wall means, said openings being substantially contiguous with said wall of said pump chamber means and conducting fluid to be pumped to said wall means and said cavity;
   (g) means for forcing said body of elastomeric material and said wall means into contact with sufficient force to cause said elastomeric material to be deformed against said wall means and substantially displace said cavity; and
   (h) pressure activated valve means in communication with said passage means for allowing unidirectional flow of said fluid from said cavity through said probe means in response to fluid pressure generated upon displacement of said cavity.

2. A pump mechanism as recited in claim 1, wherein: said housing means is formed to define fluid shear means in juxtaposition with said inlet opening, said fluid shear means preventing the development of fluid turbulence at said inlet opening.

3. A pump mechanism as recited in claim 2, wherein: said fluid shear means is defined by a pair of elongated generally knife-edged lips positioned at opposed sides of said inlet opening.

4. A pump mechanism as recited in claim 1, wherein said body of fluid is flowing fluid contained within a pipeline and said pump mechanism includes:
   means for securing said probe means in assembly with said pipeline with said free extremity of said transducer housing means in communication with fluid flowing through said pipeline, said probe means being movably positionable relative to said pipeline for selective location of said wall means within said pipeline.

5. A pump mechanism as recited in claim 4, wherein said probe means comprises:
   (a) an outer tubular member;
   (b) said transducer housing being secured to one extremity of said outer tubular member, said transducer housing defining one extremity being supported by said outer tubular member and defining a free extremity, said wall means defining said free extremity of said transducer housing;
   (c) an inner tubular member being movably disposed within said outer tubular member and defining at least a part of said flow passage means; and
   (d) said elastomeric body being disposed within said transducer housing and being moved relative to said wall means by said inner tubular member.

6. A pump mechanism as recited in claim 4, wherein said probe means further comprises:
   (a) anvil means being secured to one extremity of said inner tubular member;
   (b) support means being movably secured to said anvil means and adapted for limited linear movement relative thereto; and
   (c) said resilient body being retained by said support means.

7. A pump mechanism as recited in claim 6, wherein pressure actuated valve means in supported by said inner tubular member and having an inlet in communication with said cavity and an outlet in communication with said passage means, said pressure activated valve means allowing fluid flow therethrough only at a selected minimum pressure exceeding the maximum pressure of fluid within said pipeline.

8. A pump mechanism as recited in claim 7, including: a substantially rigid tube defining said passage means of said body of elastomeric material, said tube being supported by said anvil and defining a part of said inlet of said relief valve means, said tube extending through said elastomeric body and having one end thereof positioned within said cavity.

9. A fluid pump mechanism for pumping measured samples from a desired position within a pipeline with minimal interference to the flow of fluid through the pipeline, said fluid pump mechanism comprising:
  (a) sampling probe means having an extremity that is extendable into said pipeline, said sampling probe means being defined by an outer tubular member having an inner tubular member disposed for reciprocation therein, said inner tubular member defining flow passage means;
  (b) a sample collection housing having one extremity thereof connected to said outer tubular member of said sampling probe and having a pump wall defining a free extremity of said housing, said sample collection housing defining an internal chamber with said pump wall at said free extremity, said sample collection housing further defining opposed elongated inlet and outlet opening means in juxtaposition with said wall;
  (c) an elastomeric body being supported by said inner tubular member and being movably positioned within said internal chamber and defining a pumping cavity opening toward said pump wall, said elastomeric body being deformable against said wall to the extent that the elastomeric material of said elastomeric body completely displaces said cavity;
  (d) unidirectional valve means being positioned in communication with said flow passage means of said inner tubular member and opening responsive to pressure generated upon displacement of said pumping cavity to permit the flow of fluid from said pumping cavity to said flow passage means of said inner tubular member;
  (e) pump passage means extending through said elastomeric body and communicating with said pumping cavity and said valve means, upon displacement of said pumping cavity by said elastomeric material, fluid contained within said pumping cavity being forced through said passage means; and
  (f) means for selectively moving said elastomeric body within said internal chamber and imparting sufficient force to deform said elastomeric body against said wall.

* * * * *